(12) United States Patent
Allard et al.

(10) Patent No.: US 12,391,447 B2
(45) Date of Patent: Aug. 19, 2025

(54) MODULAR PACKAGING STRUCTURES

(71) Applicant: ECA Medical Instruments, Inc., Thousand Oaks, CA (US)

(72) Inventors: Randall Allard, Thousand Oaks, CA (US); Philippe Pare, Thousand Oaks, CA (US)

(73) Assignee: ECA Medical Instruments, Thousand Oaks, CA (US)

( * ) Notice: Subject to any disclaimer, the term of this patent is extended or adjusted under 35 U.S.C. 154(b) by 148 days.

(21) Appl. No.: 17/824,822

(22) Filed: May 25, 2022

(65) Prior Publication Data

US 2022/0380105 A1 Dec. 1, 2022

Related U.S. Application Data

(60) Provisional application No. 63/192,960, filed on May 25, 2021.

(51) Int. Cl.
*B65D 75/36* (2006.01)
*A61B 50/30* (2016.01)

(52) U.S. Cl.
CPC ............ *B65D 75/367* (2013.01); *A61B 50/30* (2016.02)

(58) Field of Classification Search
CPC .............................. B65D 75/367; A61B 50/30
USPC .................................. 206/495, 499, 483, 477
See application file for complete search history.

(56) References Cited

U.S. PATENT DOCUMENTS

| | | | | |
|---|---|---|---|---|
| 3,780,854 A * | 12/1973 | Ruppenthal | ........... | B65B 27/083 248/346.02 |
| 5,363,956 A * | 11/1994 | Taniyama | .......... | G11B 33/0416 206/483 |
| 5,762,191 A * | 6/1998 | Etzion | ................ | B65D 73/0014 206/487 |
| 5,772,039 A * | 6/1998 | Orr | ........................ | A47F 7/024 206/460 |
| 6,146,673 A * | 11/2000 | Ferguson | ............. | B65D 25/108 220/660 |
| 6,153,237 A * | 11/2000 | Ferguson | ............. | B65D 25/108 220/660 |
| 6,193,066 B1 * | 2/2001 | Kilmartin, III | ........ | A45C 11/16 206/495 |
| 6,915,901 B2 * | 7/2005 | Feinberg | .......... | A61B 17/00491 206/363 |
| 6,991,097 B1 * | 1/2006 | Sheehan | ................. | B23P 21/00 206/499 |

(Continued)

*Primary Examiner* — Jacob K Ackun
(74) *Attorney, Agent, or Firm* — Ferguson Case Orr Paterson

(57) ABSTRACT

Described herein are modular packaging structures and corresponding packaging methods. Packaging structures incorporating features of the present disclosure can comprise a base structure, for example a tray comprising a volume, and a backer card, which can be configured to receive one or more objects to be packaged. Differently designed backer cards can be utilized with the same base structure allowing for a modular packaging structure and preventing the need for specialized and specifically tooled trays for different products. The backer cards may interact with the base structures to form multiple compartments. These modular packaging structures allow for a great level of customizability and help mitigate the cost and labor typically required in utilizing multiple specifically tooled thermoform trays.

11 Claims, 3 Drawing Sheets

(56) References Cited

U.S. PATENT DOCUMENTS

| | | | | |
|---|---|---|---|---|
| 7,377,390 | B2* | 5/2008 | Modesto | A47F 7/00 |
| | | | | 206/464 |
| 7,987,978 | B1* | 8/2011 | Lam | A45C 11/00 |
| | | | | 206/483 |
| 8,220,636 | B2* | 7/2012 | Beecroft | B65D 83/0472 |
| | | | | 206/499 |
| 2003/0017234 | A1* | 1/2003 | Hentzel | B65D 5/503 |
| | | | | 206/483 |
| 2003/0213717 | A1* | 11/2003 | Kanai | B65D 81/07 |
| | | | | 206/583 |
| 2006/0157372 | A1* | 7/2006 | Pollnow | B65D 25/2844 |
| | | | | 206/483 |
| 2007/0124896 | A1* | 6/2007 | Wong | B65D 73/005 |
| | | | | 24/19 |
| 2007/0209956 | A1* | 9/2007 | Perkins-Stanaford | ........................ |
| | | | | B65D 77/046 |
| | | | | 206/495 |

* cited by examiner

MODULAR PACKAGING STRUCTURES

This application claims the benefit of U.S. Provisional Patent Application Ser. No. 63/192,960, filed on May 25, 2021. The application referred to in this paragraph is incorporated by reference as if set forth fully herein.

BACKGROUND

Related Field

The present disclosure relates generally to packaging, and specifically, to hybrid packaging structures utilizing, for example, molded tray portions and backer cards in the use of packaging medical instruments and devices.

Description of the Related Art

Conventional packaging structures, particularly in fields requiring the packaging of many small particularly-shaped objects, for example, in the field of medical devices and instruments, can be costly to manufacture, often requiring thermoformed trays with intricately tooled pockets with dimensions configured to hold and secure the various medical devices and instruments for a particular "kit." For example, one packaging structure may comprise a tray with tooled pockets corresponding to the shape and size of particular hemostats, clamps, and stitching equipment forming a vascular surgery kit, while another packaging structure may comprise tooled pockets corresponding to the shape and size of particular bone screws, screwdrivers and trocar devices forming an orthopedic surgery kit.

For a company that manufactures multiple kits or other packaged compilations of items of a sufficient variety, the process of manufacturing multiple variations of thermoformed trays with multiple pockets of varying dimensions requiring extensive tooling is costly both in terms of machine cost and manufacturing throughput efficiency. These conventional packaging systems require multiple separate trays to accommodate the variety of products the company sells.

Accordingly, a packaging structure that would allow for inexpensive and efficient customization allowing for use with a variety of objects corresponding to different products would be advantageous over these conventional packaging systems.

SUMMARY

Described herein are modular packaging structures and methods involving packaging structures comprising for example, a base structure, a tray, and an interchangeable backer card configured to receive and hold one or more objects. The base structure can be configured to receive the backer card allowing for a universal base structure that does not require customized tooling and or limit the package to a particular use. The base structure can be utilized with various backer card configured to accommodate a variety of different objects which may be organized into kits.

In one embodiment, a packaging structure comprises a backer card configured to receive and retain one or more objects and a base structure comprising a floor and one or more walls, wherein the base structure is configured to receive the backer card.

In another embodiment, a packaging structure comprises a backer card configured to receive one or more objects, with the backer card comprising at least two regions configured to be moveable in relation to one another along at least one fold-line, and a tray comprising a volume, wherein the tray is configured to receive the backer card.

In yet another embodiment, a method of packaging one or more objects comprises providing a base structure having a floor and one or more walls, wherein the base structure is configured to receive a backer card. The backer card is then provided and comprises one or more retainment features configured to facilitate connection of the backer card to one or more objects. At least one object is connected to the backer card which is then connected to the base structure.

These and other further features and advantages of the disclosure would be apparent to those skilled in the art from the following detailed description, taken together with the accompanying drawings, wherein like numerals designate corresponding parts in the figures, in which:

DETAILED DESCRIPTION

Figure 1:
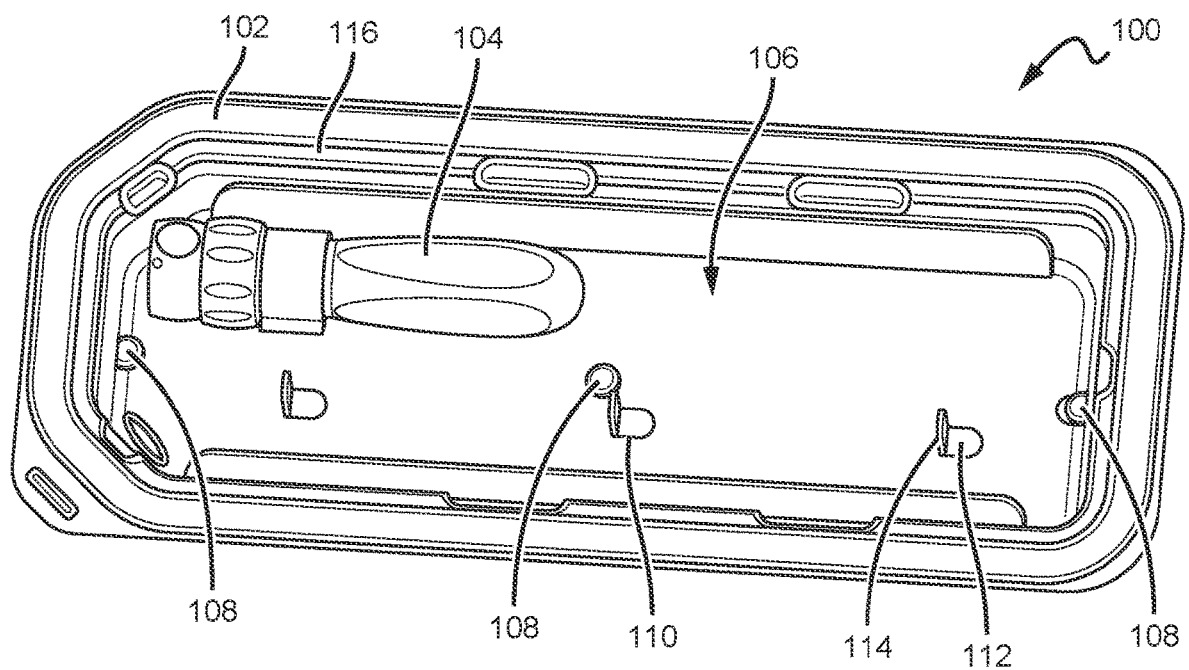
FIG. 1 shows a top perspective view of a packaging structure incorporating features of the present disclosure.

In the following detailed description, numerous specific details are set forth in order to provide a more thorough understanding of embodiments incorporating features of the present disclosure. However, it will be apparent to one skilled in the art that devices and methods according to the present disclosure can be practiced without necessarily being limited to these specifically recited details.

Embodiments incorporating features of the present disclosure can comprise a packaging structure comprising a universal base structure, for example a tray defining a partially enclosed volume to contain objects to be packaged therein. These base structures can be configured to receive one or more backer cards.

In some embodiments, the backer cards can comprise cheaper or more flexible materials than the base structures. In this way, a company needing packaging sufficient to protect objects by retaining them in position to prevent movement and sliding during transport can utilize a single base structure than can be modularly configured with specifically designed backer cards customized for different sets of objects. This can eliminate the need for specifically tooled base packaging structures designed for particular objects, allowing a company to tool up a universal base structure for use in combination with customized backer cards. Thus, these packaging structures can result in increased manufacturing efficiency and reduced material/labor costs.

Throughout this description, embodiments and examples illustrated should be considered as exemplars, rather than as limitations on the present disclosure. As used herein, the term "invention," "device," "method," "present invention," "present device," or "present method" refers to any one of the embodiments of the disclosure described herein, and any equivalents. Furthermore, reference to various feature(s) of the "invention," "device," "method," "present invention," or "present device," or "present method" throughout this document does not mean that all claimed embodiments or methods must include the referenced feature(s).

Furthermore, any element in a claim that does not explicitly state "means for" performing a specified function, or "step for" performing a specific function, is not to be interpreted as a "means" or "step" clause as specified in 35 U.S.C. § 112, for example, in 35 U.S.C. § 112(f) or pre-AIA 35 U.S.C. § 112, sixth paragraph. In particular, the use of "step of" or "act of" in the claims herein is not intended to invoke the provisions of 35 U.S.C. § 112.

It is also understood that when an element or feature is referred to as being "on" or "adjacent" to another element or feature, it can be directly on or adjacent the other element or feature or intervening elements or features may also be present. It is also understood that when an element is referred to as being "attached," "connected" or "coupled" to another element, it can be directly attached, connected or coupled to the other element or intervening elements may be present. In contrast, when an element is referred to as being "directly attached," "directly connected" or "directly coupled" to another element, there are no intervening elements present.

Please note, if used, relative terms such as "left," "right," "front," "back," "top," "bottom," "forward," "reverse," "clockwise," "counter-clockwise," "outer," "inner," "above," "upper," "lower," "below," "Horizontal," "vertical," and similar terms, have been used for convenience purposes only and are not intended to imply any particular fixed direction. Instead, they are used to reflect relative locations and/or directions between various portions of an object.

Although ordinal terms, e.g., first, second, third, etc., may be used herein to describe various elements or components, these elements or components should not be limited by these terms. These terms are only used to distinguish one element or component from another element or component. Thus, a first element or component discussed below could be termed a second element or component without departing from the teachings of the present disclosure.

The terminology used herein is for describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," when used herein, specify the presence of stated features, integers, steps, operations, elements, and/or components, but do not preclude the presence or addition of one or more other features, integers, steps, operations, elements, components, and/or groups thereof.

Embodiments of the disclosure are described herein with reference to different views and illustrations that are schematic illustrations of idealized embodiments of the disclosure. As such, variations from the shapes of the illustrations as a result, for example, of manufacturing techniques and/or tolerances are expected. Embodiments of the disclosure should not be construed as limited to the particular shapes of the regions illustrated herein, but are to include deviations in shapes that result, for example, from manufacturing.

It is understood that when a first element is referred to as being "between" or "interposed between" two or more other elements, the first element can be directly between the two or more other elements or intervening elements may also be present between the two or more other elements. For example, if a first element is "between" or "interposed between" a second and third element, the first element can be directly between the second and third elements with no intervening elements, or the first element can be adjacent to one or more additional elements with the first element and these additional elements all between the second and third elements.

FIG. 1 shows a packaging structure 100 comprising a base structure 102, which can comprise a floor and one or more walls (four shown). In the embodiment shown in FIG. 1, the base structure 102 comprises a tray having a volume, in which objects such as medical device 104 can be placed. While packaging structures incorporating features of the present disclosure can be utilized in conjunction with a wide variety of objects, the modular nature of the packaging devices is particularly beneficial in the field of medical device packaging. These packaging structures are modular such that multiple objects can utilize the same base structure 102, without the need of retooling the base structure 102 for every particular use and object. Additionally, because the packaging structures are inexpensive and efficiently manufactured, the packaging structures are particularly well-suited for use with sterile and single-use medical instruments and devices.

Although a rectangular tray is shown in FIG. 1, the base structure 102 can comprise any suitable shape capable of receiving a backer card, such as the backer card 106 shown in FIG. 1. In some embodiments, the base structure 102 comprises a floor and at least one wall. In some embodiments, the base structure 102 comprises a tray structure defining a volume in which the backer card 106 and objects for packaging can be placed. While the base structure 102 has a roughly rectangular shape with curved edges, a floor portion, and four interior wall portions, it is understood that the base structure 102 can comprise any other suitable shape, for example, a shape of any regular or irregular polygon and can have volumes designed to accommodate any particular application.

The base structure 102 can comprise any suitable material capable of performing its function as a base packaging structure including, but not limited to: resin, rubber, vinyl, polyurethane, polyvinyl chloride (PVC), polystyrene foam, polymers/copolymer substances, acrylic substances, plastic, leather, metal, wood, Polytetrafluoroethylene (PTFE), often marketed under the brand name Teflon®, nylon polymers, polyetherimide), often marketed under the brand name Ultem®, polyetherimide with glass, polyetherimide with nylon, polyetherimide with PTFE, polyetheretherketone, polyetheretherketone with glass, polyetheretherketone with carbon, thermal plastics, or combinations thereof. In some embodiments, the base structure 102 comprises a thermoform plastic. In other embodiments, the base structure 102 comprises a translucent, transparent or semitransparent material, with a potential advantage of these embodiments being the packaged objects within can be readily viewed through the packaging. The base structure may also comprise translucent portions in combination with opaque portions. For example, such a combination would allow for the contents to be visible through certain portions of the base structure (i.e., the translucent portions) while allowing for printing on other portions of the base structure (i.e., the opaque portions).

The base structure 102 can be configured to receive a backer card 106 in a variety of ways, for example, the area defined by the floor and walls of the base structure can correspond to the shape and/or size of the backer card 106 to hold it snugly in place. It is possible to taper the interior walls so that the backer card 106 can be press-fit against the floor of the base structure 102. In some embodiments, the base structure 102 can be configured to receive the backer card 106 using one or more card-connection features 108 (three shown) configured to facilitate connection of the backer card 106 to the base structure 102. These card-connection features 108 can comprise any structure configured to connect the backer card 106 to the base structure 102, for example, adhesive structures, hooks, and structures configured to mate with complementary structures, such as shown in FIG. 1, wherein the base structure 102 comprises card-connection features 108 in the form of protruding structures that mate with corresponding indentations on the backer card 106. In other embodiments, similar card-connection features can be used to align the backer card within the base structure, or they can be used as polarity indicators to ensure that the backer cards are connected to the base structure in a particular orientation.

The backer card 106 itself can comprise any suitable shape or material enabling the backer card 106 to perform the function of securing and/or connecting to objects, for example, any of the shapes and materials listed in reference to the base structure 102 above. In some embodiments, the backer card 106 comprises a size and shape allowing the backer card 106 to be at least partially surrounded by portions of the base structure 102, for example, the backer card 106 can be received by the base structure 102 such that it rests on the floor of the base structure and is surrounded by the walls of the base structure 102, for example, resting within the defined volume of a tray-like base structure 102 as shown in FIG. 1.

The backer card 106 can further comprise retainment features 110 (three shown). The retainment features 110 are configured to facilitate connection of the backer card 106 to one or more objects and can comprise any suitable shape, structure and configuration to perform this function, for example, an adhesive, or a hook-like or loop-like structure that can help engage with an object to hold it in place. In the embodiment shown in FIG. 1, the retainment features 110 comprise an indentation 112 and a protrusion 114. In other embodiments, the retainment features 110 can comprise only one or more indentations 112, only one or more protrusions 114 or other suitable connection-facilitating structures altogether. The indentations 112 and protrusions 114 can directly connect to an object with corresponding features, or can be utilized with tie-down structures, such as string, zip-ties, or twist-ties to help securely fasten objects to the backer card 106.

Once objects to be packaged have been connected/fastened to the backer card 106, the backer card 202 may be inserted into the base structure 102. In some embodiments, the open end of the base structure is then sealed for storage and transportation. The sealing material can be a thin sheet of plastic, for example. The sealing material may also be a more durable material such as a polyethylene sheet, commercially available as Tyvek®. Other seal materials may also be used. In some embodiments, the backer card and the objects therein will be arranged within the base structure so that when the seal material is removed, the objects can be dumped onto a sterile surface without the need to touch them. In other embodiments, the objects may be connected/fastened to the backer card so that when the seal is removed the backer card itself along with the objects fastened to it can be dumped out of the base structure and onto a sterile surface.

FIG. 1 further shows that the base structure 102 can be configured to receive one or more additional backer cards. In the case of FIG. 1, the base structure 102 comprises a lip portion 116 upon which a second backer card 202 (shown in FIG. 2) can rest and/or be held in place.

Figure 2:
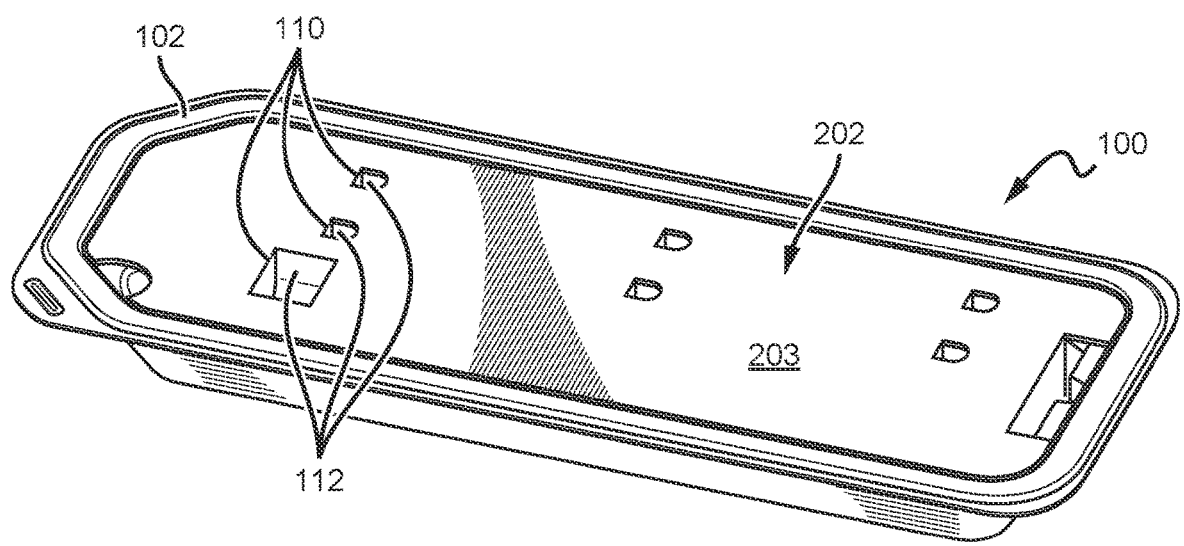
FIG. 2 shows a top perspective view of the packaging structure of FIG. 1 with a second backer card incorporated in the top-portion of the packaging structure.

FIG. 2 shows the embodiment of FIG. 1, with a second backer card 202 connected to the base structure 102 of the packaging structure 100. The lower backer card 106 and some of the other features from FIG. 1 can not been seen clearly in FIG. 2 as they are obscured by the second backer card 202 in this view. Like the lower backer card 106, the second backer card 202 comprises retainment features 110 configured to facilitate connection of the backer card 202 to one or more objects. The particular retainment features 110 of the second backer card 202 comprise indentations 112, similar to the indentations 112 shown in FIG. 1.

As previously mentioned, the packaging structure 100 may be sealed once the contents are placed inside. For example, in some embodiments, a lid portion or retaining lid (not shown in FIG. 2) can connect to and/or be an intrinsic part of the base structure 102 to function as the seal. This lid portion can abut the back side surface 203 of the backer card 202. For example, in the embodiment shown in FIG. 2, a lid structure can connect to the top portion of the body 102 and therefore be positioned over the back side surface 203 of backer card 202. In some embodiments, the lid structure can form a protective seal with the base structure 102, which can be particularly advantageous in embodiments wherein a sterile product, such as a medical instrument or device is to be packaged. In some embodiments, this seal is moisture proof. In some embodiments, this seal is hermetic. In these embodiments, utilizing a lid structure as a protective seal, the back side surface 203 of the backer card 202, visible in FIG. 2, can comprise a substantially flat and/or smooth surface against the lid structure. Such a smooth surface can help prevent the backer card 202 from significantly interfering with the protective seal. Furthermore, the smooth back side surface 203 of the backer card 202 will distribute weight and pressure of the internal contents more evenly across the entire surface of the lid portion and will ensure that the contents do not push up against the lid portion directly, forcing an edge of the lid portion open or puncturing it completely.

Figure 3:
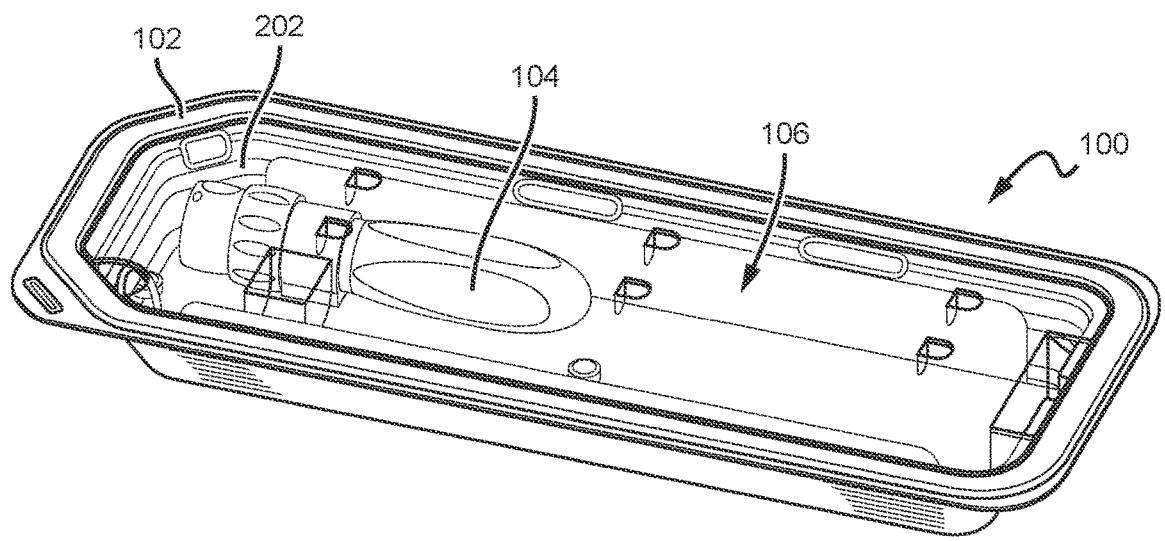
FIG. 3 shows the top perspective view of the packaging structure of FIG. 2 with the second backer card shown in transparent view to enhance visualization.

Additional features of the packaging structure 200 of FIG. 2 can be seen in FIG. 3, which shows the second backer card 202 comprising a transparent material allowing the lower backer card 106 and the medical device 104 from FIG. 1 to be seen more clearly. The view shown in FIG. 3 also shows that the packaging device 100 can comprise multiple compartments defined by the interaction of the base structure 102 with the lower backer card 106 and the second backer card 202. In the embodiment shown, there are two such compartments providing areas to retain objects such as the medical device 104: a first compartment located above the lower backer card 106 and below the second backer card 202 and a second compartment located above the second backer card 202, which can function as an upper deck to which additional objects can be connected. In this way, multiple compartments can be created within the base structure 102. In this particular embodiment, there are two separate compartments; however, it is understood that additional compartments can be created by stacking similar structures. It is possible to create as many separate compartments as necessary for a particular application.

Figure 4:
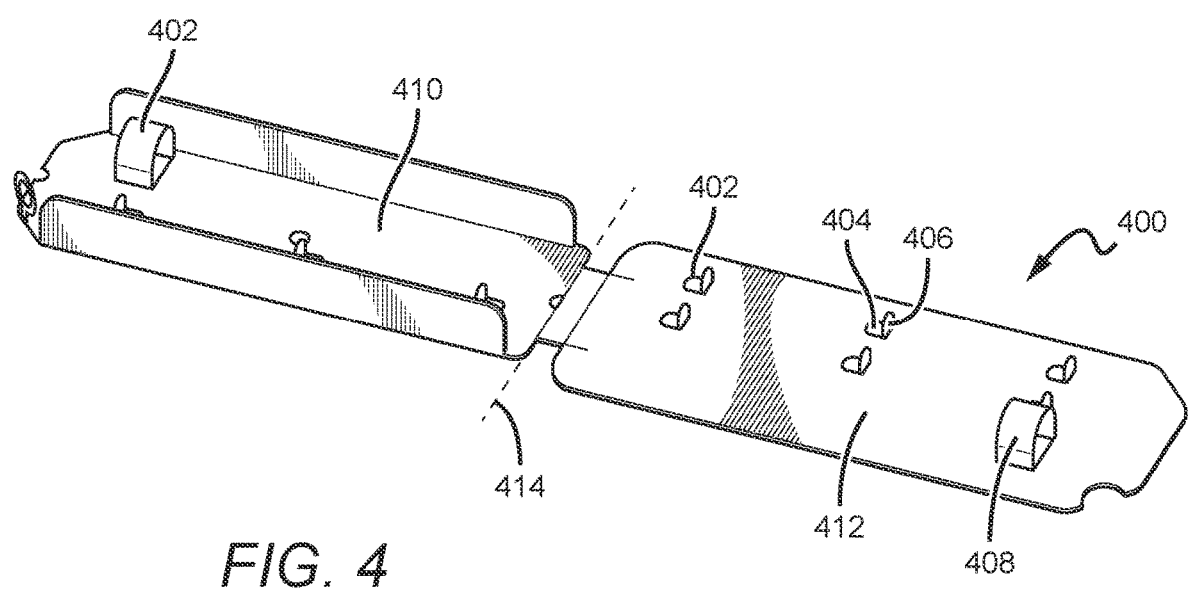
FIG. 4 shows an embodiment of a backer card incorporating features of the present disclosure.
Figure 5:
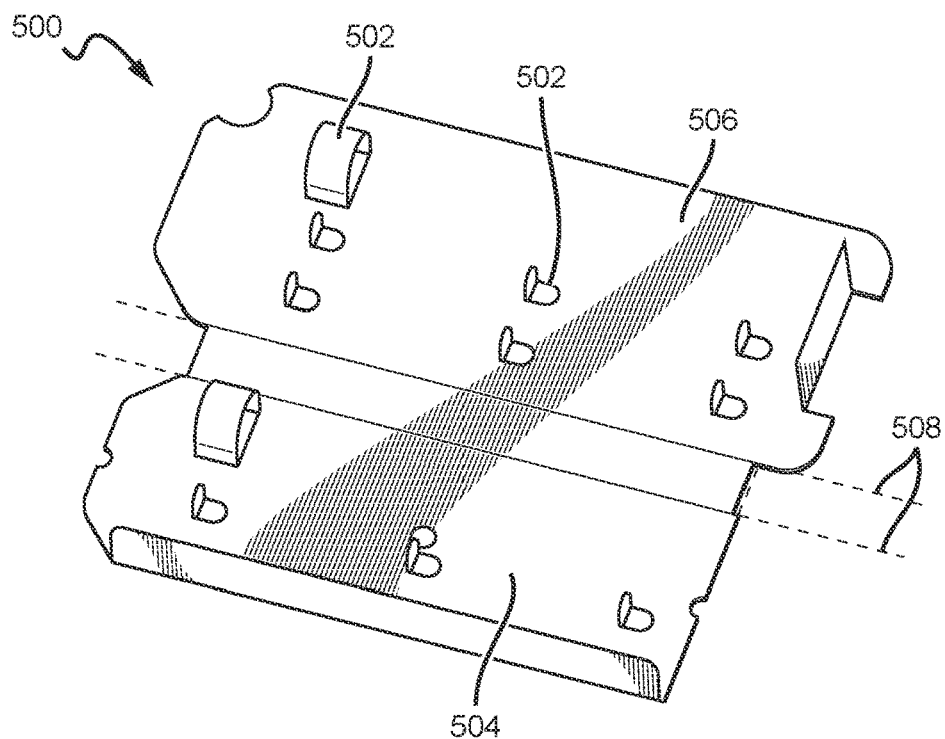
FIG. 5 shows another embodiment of a backer card incorporating features of the present disclosure.
Figure 6:
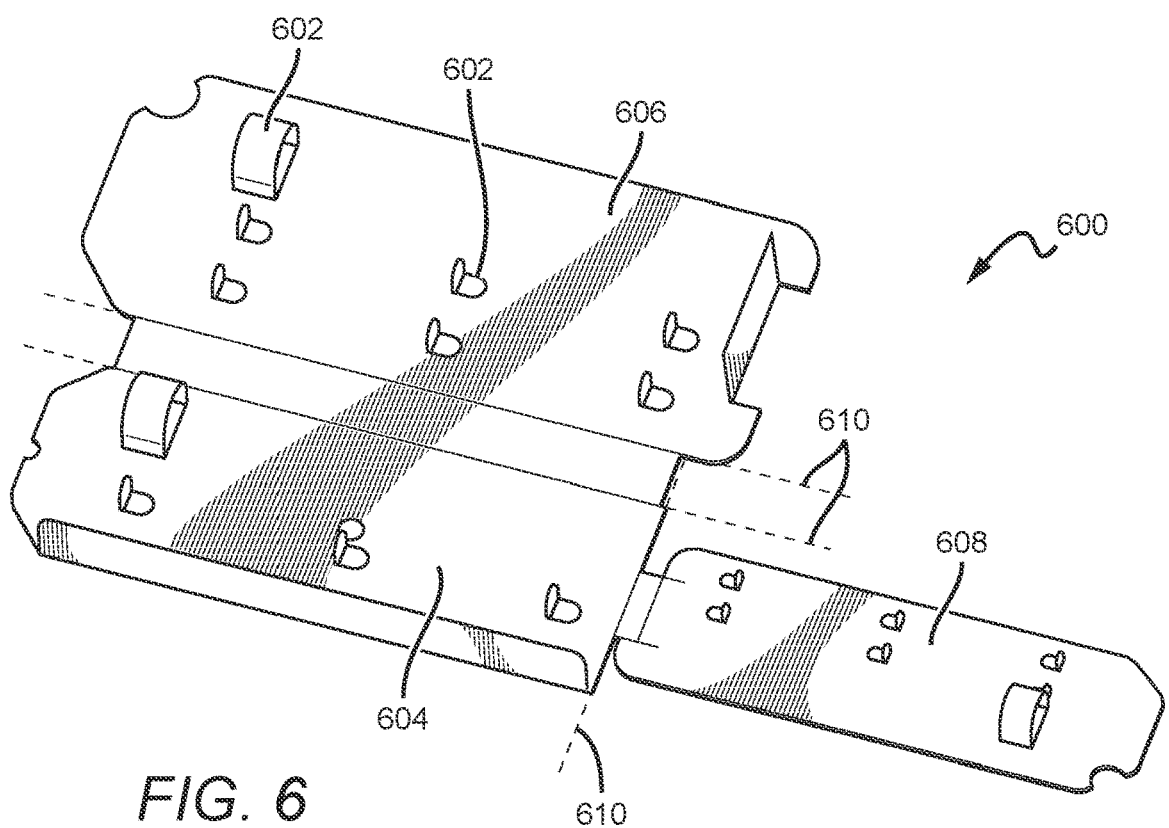
FIG. 6 shows yet another embodiment of a backer card incorporating features of the present disclosure.

In some embodiments, a single backer card can be configured to allow for the formation of multiple compartments within the packaging device 100. Examples of such backer cards are shown in FIGS. 4-6. FIG. 4 shows a backer card 400, comprising retainment structures 402, similar to the retainment structures 110 shown in FIG. 1.

The retainment structures 402 comprise indentations 404, and protrusions 406, like the indentations 112 and protrusions 114 in FIG. 1. This embodiment also comprises a loop structure 408 configured to fit around a portion of an object to be connected to the backer card 400, such as the handle of a surgical tool, for example. Other embodiments may include a tie-down structure to fasten objects to one of the backer cards.

The backer card 400 further differs from the backer cards 106, 202 of FIGS. 1-3 above in that the backer card 400 comprises two distinct regions, a first region 410 and a second region 412. In the embodiment shown in FIG. 5, the first region 410 and the second region 412 are configured to be folded such that regions 410, 412 are substantially parallel with one another within the footprint of a corresponding base structure. For example, in the embodiment shown, the backer card 400 comprises a relatively flexible material such as cardboard and can bend along a pivot point 414 (e.g., a fold line, a score line, or a living hinge). In some embodiments various joint-like structures, such as hinges or ball-and-socket joints can be utilized to allow the first region 410 of the backer card 410 to move in relation to the second region 412, and vice versa. In this embodiment, the backer card 410 is foldable along a transverse fold line at the pivot point 414.

FIG. 5 shows another embodiment of a backer card 500, similar to the backer card 400 in FIG. 4. The backer card 500 comprises retainment structures 502. The backer card 500 further comprises two distinct regions, a first region 504 and a second region 506. The first region 504 and the second region 506 are configured to be moveable (e.g., by folding) in relation to one another, similarly as regions 410, 412. The backer card 500 of FIG. 5 can comprise one or more pivot points 508 (two shown), similar to the pivot point 414, that enables the first region 504 and the second region 506 to be folded into a substantially parallel configuration within the footprint of a corresponding base structure. As shown in FIG. 5, various retainment features 502 on the first region 504 can be staggered in relation to corresponding retainment features 502 on the second region 506 so that when the backer card 500 is the folded configuration, the retainment features 502 of various regions will not interfere with one another. This also allows for objects to be stored on both regions 502, 504 within the same compartment. In this embodiment, the backer card 500 is foldable along two longitudinal fold lines at the pivot points 508.

FIG. 6 shows another embodiment of a backer card 600, similar to the backer card 500. The backer card 600 comprises retainment structures 602, similar to the retainment structures 502. The backer card 600 differs from the backer card 500 in that it comprises three distinct regions, including a first region 604, a second region 606, and a third region 608. The first region 604 and the second region 606 are configured to be folded into a substantially parallel configuration, similarly as regions 410, 412 in FIG. 4. Additionally, the second region 606 and the third region 608 are likewise configured to be folded into a substantially parallel configuration with one another. Thus, all three regions 604, 606, 608 can be folded into a parallel configuration within the footprint of a base structure. In this embodiment, the backer card 600 is foldable along transverse and longitudinal fold lines at the pivot points 610.

It is understood that the features of one embodiment can be combined with the features of another embodiment. For example, an embodiment can comprise backer cards with retainment structures and multiple regions foldable in relation to one another in many different configurations. Thus, it is possible to create a structure with multiple separate compartments within the same base structure. Multi-tiered backer cards may fold in many different ways to create as many discrete compartments as required by a particular application. The backer cards can remain in a flat configuration for efficient storage/transportation prior to use.

Although the present disclosure has been described in detail with reference to certain preferred configurations thereof, other versions are possible. Embodiments of the present disclosure can comprise any combination of compatible features shown in the various figures, and these embodiments should not be limited to those expressly illustrated and discussed. Therefore, the spirit and scope of the disclosure should not be limited to the versions described above.

The foregoing is intended to cover all modifications and alternative constructions falling within the spirit and scope of the disclosure as expressed in any appended claims, wherein no portion of the disclosure is intended, expressly or implicitly, to be dedicated to the public domain if not set forth in the claims.

We claim:

1. A packaging structure, comprising:
   a backer card configured to secure one or more objects;
   a base structure, said base structure comprising a floor and one or more walls, wherein said base structure is configured to receive said backer card; and
   an upper backer card, wherein said backer card, said upper backer card, and said base structure interact to form multiple compartments.

2. The packaging structure of claim 1, wherein at least one of said backer card and said upper backer card is configured to secure at least one medical instrument or device.

3. The packaging structure of claim 1, wherein said base structure comprises a tray structure comprising a volume.

4. The packaging structure of claim 1, wherein at least a portion of said packaging structure comprises a transparent surface.

5. The packaging structure of claim 1, further comprising indentations.

6. The packaging structure of claim 1, further comprising protrusions.

7. The packaging structure of claim 6, wherein said one or more protrusions are configured to abut said one or more objects.

8. The packaging structure of claim 6, wherein said one or more protrusions comprise loop-like structures.

9. The packaging structure of claim 1, wherein said base structure comprises one or more card-connection features configured to facilitate connection of said backer card to said base structure.

10. The packaging structure of claim 1, wherein said backer card comprises at least two regions, said at least two regions configured to be moveable in relation to one another.

11. The packaging structure of claim 1 further comprising:
    a sealing material configured to form a seal with the edges said one or more walls opposite the floor of said base of structure.

* * * * *